(12) United States Patent
Miller et al.

(10) Patent No.: US 9,358,087 B2
(45) Date of Patent: Jun. 7, 2016

(54) ORAL HYGIENE APPLIANCE WITH FORMABLE SUBSTRATE

(75) Inventors: Kevin A. Miller, Bellevue, WA (US); Patrick A. Headstrom, Seattle, WA (US); Bethany Joyce Johnson, Snoqualmie, WA (US); Ian Gordon Blanch, Seattle, WA (US); Tijn Pieter Lodewijk Huttenhuis, Denekamp (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 450 days.

(21) Appl. No.: 13/883,679

(22) PCT Filed: Dec. 9, 2011

(86) PCT No.: PCT/IB2011/055566
§ 371 (c)(1),
(2), (4) Date: Sep. 24, 2013

(87) PCT Pub. No.: WO2012/080919
PCT Pub. Date: Jun. 21, 2012

(65) Prior Publication Data
US 2014/0011159 A1   Jan. 9, 2014

Related U.S. Application Data

(60) Provisional application No. 61/422,414, filed on Dec. 13, 2010.

(51) Int. Cl.
*A61C 17/22* (2006.01)
*A46B 3/20* (2006.01)
*A61C 17/34* (2006.01)

(52) U.S. Cl.
CPC ............... *A61C 17/228* (2013.01); *A46B 3/20* (2013.01); *A61C 17/3481* (2013.01)

(58) Field of Classification Search
CPC .. A61C 17/222; A61C 17/3481; A61C 17/22; A61C 17/16; A61C 17/228; A61C 17/349; A46B 2200/1066; A46B 13/02; A46B 3/22
See application file for complete search history.

(56) References Cited

U.S. PATENT DOCUMENTS

| | | | |
|---|---|---|---|
| 2,148,483 | A | 2/1939 | Love et al. |
| 3,939,522 | A | 2/1976 | Shimizu |
| 4,083,078 | A | 4/1978 | Shimizu |
| 4,149,815 | A | 4/1979 | Kawam |
| 5,926,898 | A | 7/1999 | Kramer |

(Continued)

FOREIGN PATENT DOCUMENTS

| | | |
|---|---|---|
| CN | 2207750 Y | 9/1995 |
| DE | 102007015951 A1 | 10/2007 |
| DE | 202009008362 U1 | 10/2009 |

(Continued)

*Primary Examiner* — Robert Scruggs

(57) ABSTRACT

The power appliance (10) for cleaning teeth includes a drive system (16) and a substrate (10) for supporting a field of bristles (14) which contact teeth for cleaning. The drive system is connected to the substrate, moving the substrate in operation to produce an action of the bristle field against the teeth. The assembly, which includes internal stiffeners (60, 62, 64) in one embodiment, has two physical states, including a first state in which the substrate is softened so as to be formable to conform to the geometry of the teeth, and a second hardened state following its conformance to the teeth in which the substrate is sufficiently rigid to effectively transmit a driving motion to the bristles.

15 Claims, 4 Drawing Sheets

(56) References Cited

U.S. PATENT DOCUMENTS

| | | |
|---|---|---|
| 6,168,434 B1 | 1/2001 | Bohm-Van Diggelen |
| 7,069,615 B2 | 7/2006 | Gavney, Jr. |
| 2004/0038172 A1 | 2/2004 | Jacobs |
| 2011/0247159 A1* | 10/2011 | Steur .................... A61C 17/222 15/167.1 |

FOREIGN PATENT DOCUMENTS

| | | |
|---|---|---|
| WO | 9831297 A2 | 7/1998 |
| WO | 2005013763 A1 | 2/2005 |
| WO | 2008135258 A2 | 11/2008 |
| WO | 2010076693 A1 | 7/2010 |
| WO | 2011077283 A1 | 6/2011 |

* cited by examiner

ORAL HYGIENE APPLIANCE WITH FORMABLE SUBSTRATE

This invention relates generally to power appliances for cleaning teeth, and more specifically concerns such an appliance which has a workpiece/bristle assembly which is conformable to individual oral anatomies.

It is well known that each individual has a unique oral (teeth) geometry; typically there will also be specific teeth areas which are difficult to clean and hence susceptible to oral disease. In order for an oral hygiene appliance, such as a toothbrush or a dental cleaning mouthpiece, to be effective in cleaning teeth, it must be able to both access all the teeth and generally conform to the oral geometry of the teeth during cleaning.

Conformance with the oral geometry of the teeth can be achieved in various ways. For instance, conformance can be accomplished by a specific bristle trim contour or extension of particular bristle portions, which is the case for certain toothbrushes. However, particular bristle tip configurations are only useful for broad categories of users, and do not have the capability of conformance with the oral geometry of individual users.

In another arrangement, conformance can be achieved by the use of a deformable bristle substrate. One way in which this is achieved is with the use of an elastomer (flexible) substrate. However, this arrangement has been found to significantly limit the ability of the drive system in a power toothbrush for instance to transmit an effective bristle motion to the bristles for cleaning of the teeth.

Hence, there is no current system which has the capability of conforming the bristle assembly for the appliance, either a toothbrush or a mouthpiece arrangement, to the teeth while also being effective in transmitting brushing motion to the teeth for effective cleaning. It would be desirable to have such a system for use in a power oral cleaning appliance.

Accordingly, there is disclosed herein an appliance for cleaning teeth, comprising: an appliance and a drive system therefor; and a substrate assembly for supporting bristles thereon, wherein the drive system is connected to the substrate assembly to produce in operation an action of the bristles against the teeth, thereby cleaning the teeth, wherein the substrate assembly has two physical states including, a first, forming state in which the substrate assembly when softened is adapted to conform to the geometry of a user's teeth, and a second, operating state in which the substrate assembly and assembly is sufficiently rigid to transmit a driving motion by the drive system to the substrate assembly and bristles thereon for cleaning of the teeth.

Figure 1:
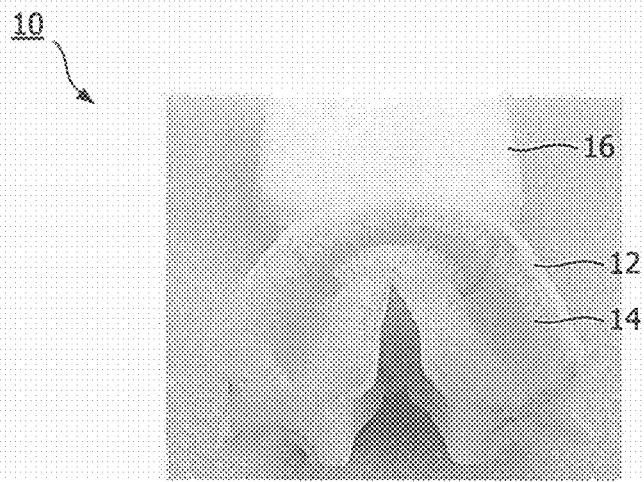
FIG. 1 shows a perspective view of a mouthpiece with the substrate/bristle arrangement disclosed herein.

FIG. 1 shows a mouthpiece embodiment of the present invention, generally at 10, which includes a substrate 12 which is arranged to receive teeth in both the upper and lower jaws. However, it should be understood that substrate 12 could be arranged to receive just the upper or lower jaw teeth. Furthermore, the substrate could be arranged to receive only selected portions of the teeth in the upper and/or lower jaws.

Positioned in substrate 12 is a bristle field, shown generally at 14. Bristle field 14 comprises a set of bristles which are suitable for brushing or cleaning teeth in a mouthpiece appliance. An example of a suitable bristle is 0.004 inch diameter nylon filament.

Mouthpiece 10 is powered by a driver arrangement shown generally at 16. Driver 16 is connected to substrate 12 in such a manner as to move the substrate and the bristle field in a motion to produce cleansing action of the teeth. The motion may be back-and-forth (in-and-out) relative to the teeth, along the teeth, rotational, a combination thereof or other motion.

Driver 16 may take various arrangements well known in the art. One such driver arrangement, for instance, is shown in PCT/IB2010/055336, owned by the assignee of the present invention, which is hereby incorporated by reference. However, it should be understood that various driving arrangements can be used with the present invention.

Substrate 12 is characterized by structural features which permit it in a first state to be able to deform and conform to the individual oral anatomy of a user, while in a second state is sufficiently rigid that it can effectively transmit brushing motion to the bristles for the driver to remove plaque; i.e. clean the teeth. This results in the significant combination of a conformable brushing appliance which is capable of adapting to the individual user's oral anatomy, while also providing an effective brushing action to produce cleansing.

Figure 7:
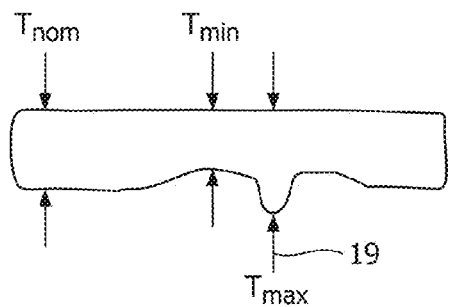
FIG. 7 is a schematic drawing illustrating the relationships between the normal and maximum and minimum thicknesses of the substrate.
Figure 8:
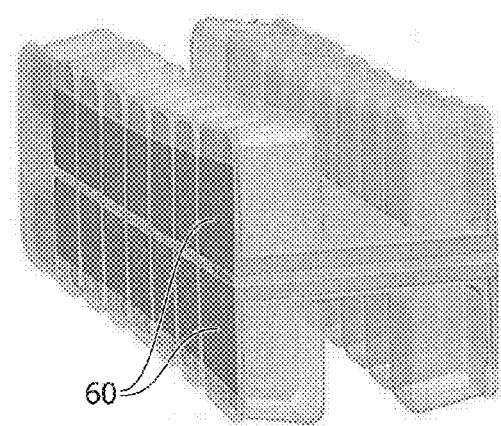
FIGS. 8-10 are perspective views of various internal stiffening members.

The material for substrate 12 is in one embodiment an ABS material known and used currently for dental forms. Alternatively, the substrate could be made of material known as T-Tape or a similar plastic, such as EVA (ethylene vinyl acetate), with a low softening point. T-Tape and similar plastics have both a very formable state and a very rigid state that uses a heat and form method that can be done in vivo to custom-form the substrate to the user's oral geometry. A generic shaped substrate of appropriate material is provided to the user. The material in the substrate provided to the user should be formable enough that it will conform to the individual surfaces of the teeth and also into the interproximal spaces thereof. In FIG. 7, the substrate 17 has a normal thickness of Tnom (2 mm) with a minimum thickness Tmin and a maximum thickness Tmax for the interproximal area, referred to at 19. Typically, the difference between the minimum thickness and the maximum thickness will be in the range of 1-4 mm, preferably greater than 1 mm. After the substrate has been formed and hardened to a rigid state, as described below, the resulting substrate should not deflect more than 50% of the drive amplitude in any part of the substrate. The above standards for the formable (flexible) state and the rigid state provide the desired results of conformance and performance for the appliance.

In the conformance process, the material in the substrate portion of the appliance is heated in boiling water until it reaches an active formable state. The substrate is then put into an individual user's mouth and aligned with the individual's oral geometry. The formable step includes two options; the bristle field with a narrow spacer may be applied to the substrate prior to the conformance step, or a spacer element may be positioned in the substrate having the same anticipated dimensions as the bristle field prior to the conformance step.

The appliance substrate is positioned with the bristles, and the user bites down on the substrate and then pushes outwardly with the tongue against the substrate to form the substrate to the inner surfaces of the teeth. The user then applies negative pressure to the mouthpiece, pulling the cheeks inwardly against the outer surface of the substrate to conform the substrate to the outer surfaces of the teeth. The substrate is then allowed to cool in that position until it hardens, which is a relatively short time, typically approximately 60 seconds.

The substrate is then removed from the mouth, at which point the spacer is removed, revealing the bristles, or alternatively, the bristle field can be attached to the substrate using various techniques, such as gluing or welding. The appliance is now ready for use, with the substrate and the bristles being conformed to the particular oral anatomy of the individual user. The driver 16 is activated when the appliance is positioned in the mouth, with the motion of the driver being transmitted to the substrate and the bristles, producing the cleansing action on the teeth, including specifically the previously indicated difficult areas of the teeth to clean. Again, for effectiveness, at least 50% of the driving motion must be transferred through the substrate to the bristles.

Figure 2:
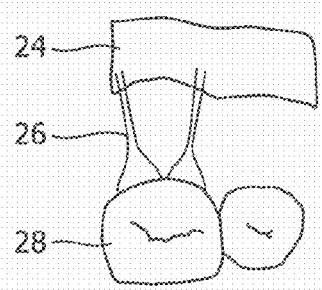
FIGS. 2 and 3 are simplified diagrams showing a portion of the substrate/bristle arrangement of FIG. 1 relative to the teeth.
Figure 3:
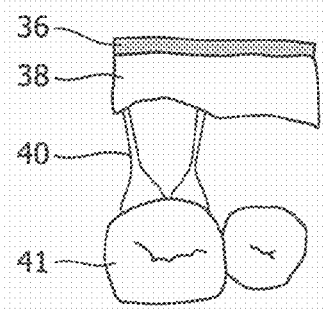

FIG. 2 shows a portion of a formable substrate 24 and bristles 26 extending therefrom to contact the teeth 28. This is the basic embodiment. FIG. 3 shows a modification of that embodiment, which includes a rigid base element 36 at the back of the formable substrate 38 with bristles 40 against teeth 4. This adds additional ridigidity to the substrate arrangement, providing increased transmission of the driving force to the bristles.

Figure 4:
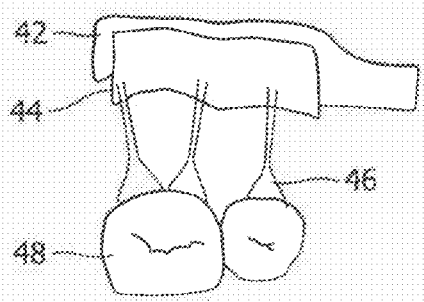
FIG. 4 is a simplified cross-sectional diagram showing the substrate/bristle arrangement disclosed herein in a toothbrush arrangement.

FIG. 4 shows an illustration of a portion of another embodiment, specifically a toothbrush. The toothbrush embodiment includes a rigid brushhead member 42, and a formable substrate 44 mounted thereon, with a bristle field 46 having an arrangement similar to a typical toothbrush. The bristle field 46 extends from the formable substrate 44 for contact with the teeth 48. Since the formable substrate will be limited in size, only the difficult areas to clean are covered by a single toothbrush. The steps of deforming the initially flexible formable substrate to conforming to the teeth and then hardening the substrate in that configuration are similar to that described above with respect to the mouthpiece. In this case, however, the toothbrush is held firmly against the individual teeth after the substrate has been heated to produce the required deformation of the substrate and arrangement of the bristles relative to particular desired areas of the teeth.

Figure 5:
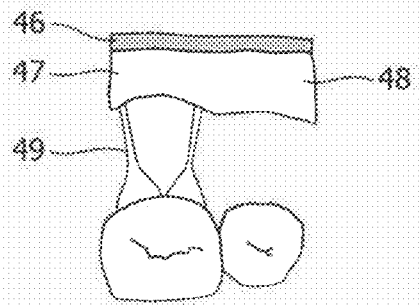
FIG. 5 is a simplified cross-sectional diagram showing a substrate/bristle arrangement which uses UV light to accomplish the desired operation of the appliance

An alternative substrate is a bladder arrangement which is filled with a liquid that can be conformed to the oral geometry of the teeth and then changed to a rigid state, such as when a UV adhesive is exposed to UV light. In this arrangement, the bladder is positioned in the mouth and aligned with the oral geometry of the teeth. The user then bites down on to the bladder. The tongue is then pushed outward against the substrate to conform to the inner surfaces of the teeth. The user then sucks and pulls the cheeks against the outer surface to conform the bladder to the outer surfaces of the teeth. The UV source is then activated to harden the liquid and the adhesive and then removed from the mouth. The spacer element is then removed from the bristles and the device is ready for use. FIG. 5 shows such an arrangement, with a rigid support member 46, a bladder substrate, comprising a membrane 47 and a liquid which is hardened to a member 48. Bristles 49 extend from the bladder.

Figure 6A:
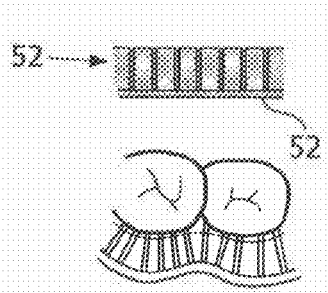
FIGS. 6A-6D show various embedding arrangements for the bristles and an accompanying shield.
Figure 6B:
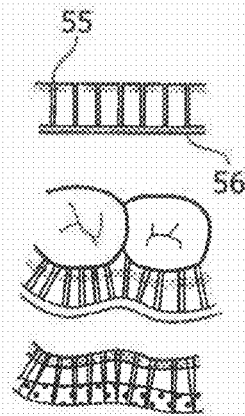
Figure 6C:
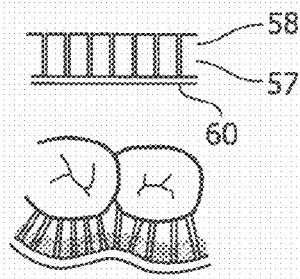
Figure 6D:
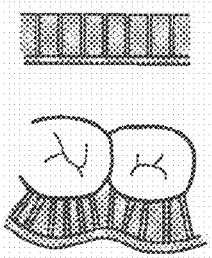

FIGS. 6A-6D show arrangements for the spacer relative to the bristles. FIG. 6A shows the bristle structure 50 fully embedded into the spacer 52. FIG. 6B shows an arrangement where only the tips 55 of bristles 51 are embedded into spacer 56. FIG. 6C shows an arrangement where only the base portion 57 of the bristles 58 is embedded into the spacer 60. FIG. 6D shows a spacer in the form of air bubbles. Of the above arrangements, FIG. 6B, with just the tips of the bristles embedded into the spacer, produces a better conformance to the teeth geometry, resulting in better coverage and brushing when the spacer is removed.

Figure 9:
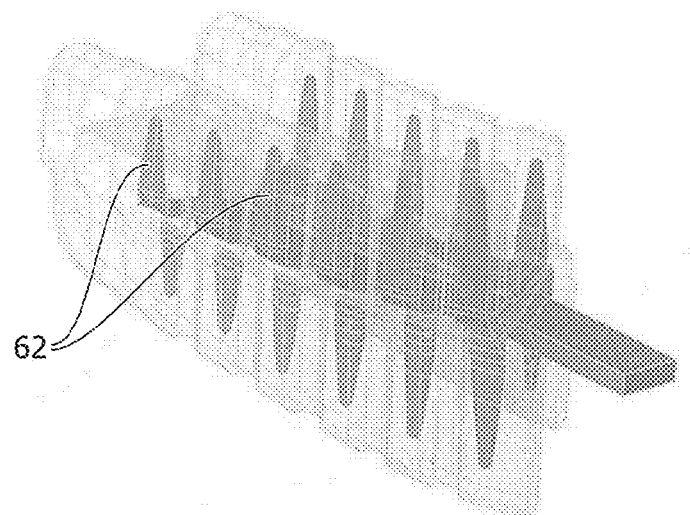
Figure 10:
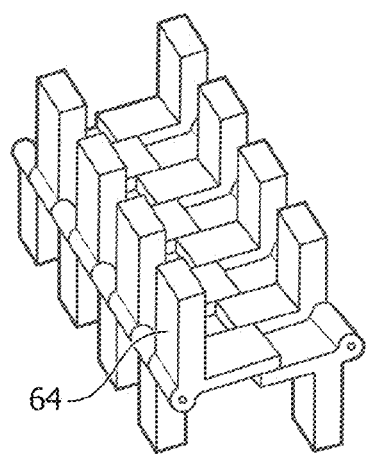

In a variation, a skeleton structure could be added internally to the formable substrate, as shown generally in FIGS. 9-11. The rigid internal structure could be thin plastic fingers 60 in FIG. 9, or flexible metal fingers 62 in FIG. 10, or H-shaped plastic fingers 64 in FIG. 11. The skeleton structure provides rigidity to the substrate while assisting in the adaption of the mouthpiece to the specific oral geometry of the individual users. The H-shaped finger can be configured to move toward and away from the user's teeth. The rigidity of the skeleton members aids in providing the necessary brushing forces for effective cleaning.

Accordingly, an oral cleaning appliance has been disclosed which includes a mouthpiece or toothbrush substrate upon which a bristle field for cleansing is mounted, wherein the substrate has two operating states. In a first state, the substrate is formable when heated so that it can conform to the unique geometry of individual user, while in a second state, the substrate is rigid, permitting good transfer of driving motion to the bristles for cleaning of the teeth. An advantage of the present arrangement is that users themselves can produce a mouthpiece or toothbrush having the desired results. Dental professionals can use the appliance as well.

Although a preferred embodiment of the invention has been disclosed for purposes of illustration, it should be understood that various changes, modifications and substitutions may be incorporated in the embodiment without departing from the spirit of the invention, which is defined by the claims which follow.

The invention claimed is:

1. An appliance for cleaning teeth, comprising:
an appliance (10) and a drive system (16) therefor; and
a substrate (12) and bristles (14) supported thereon, wherein the drive system is connected to the substrate to produce in operation an action of the bristles against the teeth, thereby cleaning the teeth, wherein the substrate has two physical states including a first, forming state in which the substrate when softened is adapted to conform to the geometry of a user's teeth, and a second, operating state in which the substrate is sufficiently rigid to transmit a driving motion by the drive system to the substrate and bristles thereon for cleaning of the teeth, wherein the substrate has such a configuration and dimensions and comprises such a material that the substrate does not deflect more than 50% of the drive amplitude in any part of the substrate when the substrate is in its second state.

2. The appliance of claim 1, wherein the appliance is a mouthpiece (10).

3. The appliance of claim 2, wherein the mouthpiece receives teeth from both upper and lower jaws.

4. The appliance of claim 2, wherein the mouthpiece appliance covers teeth from only one jaw.

5. The appliance of claim 1, wherein the appliance is a toothbrush.

6. The appliance of claim 1, wherein the substrate comprises a solid material in both the first and second states.

7. The appliance of claim 1, wherein the substrate comprises a bladder (47, 48) having a material therein which in the first state is substantially liquid and in the second state is solid and rigid.

8. The appliance of claim 1, including a layer of rigid material (36) which acts as a backing to the substrate.

9. The appliance of claim 1, including a spacer (52, 56, 60) in which at least a portion of each of the bristles is embedded when the bristles are in their first state and conformed to the geometry of the teeth following softening thereof and removable from the bristles when the substrate is in its second state.

10. The appliance of claim 9, wherein only the tips of the bristles are embedded in the spacer.

11. The appliance of claim 9, wherein only a base part of the bristles is embedded in the spacer.

12. The appliance of claim 9, wherein the entire bristles are embedded in the spacer.

13. The appliance of claim 1, wherein the substrate includes an internal stiffening member (60, 62, 64).

14. The appliance of claim 13, wherein the stiffening member is a plurality of plastic fingers or flexible metal fingers.

15. The appliance of claim 1, wherein the rigid formed substrate is configured such that the bristles have a reach into interproximal spaces of at least 1 mm.

\* \* \* \* \*